(12) United States Patent
Awaraji et al.

(10) Patent No.: US 8,589,183 B2
(45) Date of Patent: *Nov. 19, 2013

(54) PRIVACY COMPLIANT CONSENT AND DATA ACCESS MANAGEMENT SYSTEM AND METHODS

(71) Applicant: PrivIT, Inc., London (CA)

(72) Inventors: Christian Awaraji, London (CA); Pierre Awaragi, Montreal (CA)

(73) Assignee: PrivIT, Inc., London, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/626,632

(22) Filed: Sep. 25, 2012

(65) Prior Publication Data
US 2013/0263218 A1    Oct. 3, 2013

Related U.S. Application Data

(63) Continuation of application No. 11/187,834, filed on Jul. 25, 2005, now Pat. No. 8,275,632.

(60) Provisional application No. 60/590,331, filed on Jul. 23, 2004.

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC .......................................... 705/2–3
See application file for complete search history.

(56) References Cited

U.S. PATENT DOCUMENTS

| | | | |
|---|---|---|---|
| 6,314,425 B1 * | 11/2001 | Serbinis et al. | 1/1 |
| 6,651,060 B1 * | 11/2003 | Harper et al. | 1/1 |
| 7,100,206 B1 * | 8/2006 | Pere | 726/26 |
| 2003/0233357 A1 * | 12/2003 | Merenda et al. | 707/5 |
| 2004/0117215 A1 * | 6/2004 | Marchosky | 705/3 |
| 2005/0187787 A1 * | 8/2005 | Tomlinson et al. | 705/2 |
| 2005/0197859 A1 * | 9/2005 | Wilson et al. | 705/2 |

* cited by examiner

*Primary Examiner* — Joseph Burgess
(74) *Attorney, Agent, or Firm* — Greenberg Traurig LLP

(57) ABSTRACT

An information management system for restricting access to personal data in compliance with law or regulation includes a database having restricted records stored therein, at least one of the records including an identification of a client or group of clients about whom said record concerns. A computer system under the control of a trusted information broker is configured to receive via a communication medium a request initiated by a requestor for access to at least one of the restricted records in the database, the request including an identification of the requestor. The computer system is further configured to transmit a request for consent to the client and receive an indication from the client that the client consents or does not consent to access to the restricted record by the requestor. The computer system grants or denies access to the restricted records based upon the indication from the client.

20 Claims, 8 Drawing Sheets

PRIVACY COMPLIANT CONSENT AND DATA ACCESS MANAGEMENT SYSTEM AND METHODS

This application is a continuation of U.S. patent application Ser. No. 11/187,834, filed Jul. 25, 2005, entitled PRIVACY COMPLIANT CONSENT AND DATA ACCESS MANAGEMENT SYSTEM AND METHODS, which claims priority to U.S. Provisional Patent Application No. 60/590,331, filed Jul. 23, 2004, which are incorporated herein by reference in their entirety. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD OF THE INVENTION

The present invention relates to the field of information management, and more particularly provides a privacy compliant system and methods for managing access to data based on the data ownership's preferences.

BACKGROUND OF THE INVENTION

In response to concerns regarding information privacy and security (including, but not limited to, security breaches leading to identity theft, leaked or lost personal information), and recognizing the benefits achieved by keeping certain information private, a number of jurisdictions have enacted or proposed legislation to regulate the protection of, and access to, the personal, medical and financial information of individuals.

By way of example, the United States has enacted provisions under the Health Insurance Portability and Accountability Act to protect the confidentiality of individually identifiable health information, and new legislation has been introduced in the Senate ("The Specter-Leahy Personal Data Privacy and Security Act of 2005), to protect the confidentiality of personal information in general.

The concern for the protection of personal information is not limited to the United States. For example, the Parliament of the European Union issued a directive in 1995 ("Directive 95/46/EC of the European Parliament and of the Council of 24 Oct. 1995") regarding the protection of individual privacy in the processing of personal data, which included the following (inter alia) recitals: "Whereas data-processing systems are designed to serve man; whereas they must, whatever the nationality or residence of natural persons, respect their fundamental rights and freedoms, notably the right to privacy, and contribute to economic and social progress, trade expansion and the well-being of individuals"; and "Whereas the object of the national laws on the processing of personal data is to protect fundamental rights and freedoms, notably the right to privacy, which is recognized both in Article 8 of the European Convention for the Protection of Human Rights and Fundamental Freedoms and in the general principles of Community law; whereas, for that reason, the approximation of those laws must not result in any lessening of the protection they afford but must, on the contrary, seek to ensure a high level of protection in the Community."

Furthermore, by way of example, Canada has enacted legislation, referred to as Personal Information Protection and Electronic Documents Act ("PIPEDA"). PIPEDA's stated purpose is to "establish, in an era in which technology increasingly facilitates the circulation and exchange of information, rules to govern the collection, use and disclosure of personal information in a manner that recognizes the right of privacy of individuals with respect to their personal information and the need of organizations to collect, use or disclose personal information for purposes that a reasonable person would consider appropriate in the circumstances."

Even state, territory, and local governments are recognizing the need to address privacy issues. For example, Alberta, Canada, has passed the Health Information Act, which provides individuals with the right to request access to their health records in the custody or under the control of a custodian, while providing custodians with a framework within which they must conduct the collection, use and disclosure of health information. Similarly, Manitoba, Ontario and Quebec, Canada's Health Privacy Information Acts provide rights for individuals to access their personal health information and protects individual privacy rights based on the Canadian Standards Association "Fair Information Practices".

Common to the laws enacted or proposed by the jurisdictions referred to above, are a number of fundamental provisions regarding the collection, use or disclosure of personal information including, but not limited to: requirements that entities maintaining personal data establish policies to protect such data; requirements that entities maintaining personal data establish policies to regulate access to such data; requirements permitting individuals access to, and the opportunity to correct, any personal information held by entities; and requirements that entities maintaining personal data give notice to individuals regarding a breach involving such personal data.

By way of example, the privacy of personal health information is of fundamental importance to individuals.

Health plans, hospitals, pharmacies, doctors and other health care entities generally have used a wide array of systems to process and track health care bills and other information. Hospitals and doctors' offices may treat patients with many different types of health insurance and would have to spend time and money ensuring that each claim contains the format, codes and other details required by each insurer. Similarly, health plans spend time and money to ensure their systems can handle transactions from various health care providers and clearinghouses.

Enacted in August 1996, the Health Insurance Portability and Accountability Act ("HIPAA") was designed to make health insurance more affordable and accessible. With support from the health care industry, Congress also included provisions in HIPAA to require the Department of Health and Human Services ("HHS") to adopt national standards for certain electronic health care transactions, code sets, identifiers and the security of health information. HIPAA also set a three-year deadline for Congress to enact comprehensive privacy legislation to protect medical records and other personal health information. When Congress did not meet this deadline, HIPAA required HHS to issue health privacy regulations.

In August 2000, HHS issued final electronic transaction and code sets standards to streamline the processing of health care claims, reduce the volume of paperwork and provide better service for providers, insurers and patients. HHS adopted modifications to some of those standards in final regulations published on Feb. 20, 2003. Overall, the regulations establish standard data elements, codes and formats for submitting electronic claims and other health care transactions. By promoting the greater use of standardized electronic transactions and the elimination of inefficient paper forms, these standards are expected to provide a net savings to the health care industry of $29.9 billion over 10 years. All health care providers will be able to use the standardized transactions to bill for their services, and all health plans will be required to accept these standard electronic transactions.

All covered entities must be in compliance with the electronic transaction and code set standards as of Oct. 16, 2003. However, HHS' Centers for Medicare & Medicaid Services (CMS)—the agency charged with overseeing the implementation of these standards—issued guidance in July 2003 regarding the enforcement of the HIPAA transactions and code set standards after Oct. 16, 2003. The guidance clarified that covered entities, which make a good faith effort to comply with the standards, may implement contingency plans to maintain operations and cash flow. Specifically, as long as a health plan demonstrates a good-faith effort to come into compliance through active outreach and testing efforts, it can continue processing payments to providers using non-standard transactions.

In December 2000, HHS issued a final rule to protect the confidentiality of individually identifiable health information. The rule limits the use and disclosure of certain individually identifiable health information; gives patients the right to access their medical records; restricts most disclosure of health information to the minimum needed for the intended purpose; and establishes safeguards and restrictions regarding the use and disclosure of records for certain public responsibilities, such as public health, research and law enforcement. Improper uses or disclosures under the rule may be subject to criminal or civil sanctions prescribed in HIPAA.

After reopening the final rule for public comment, HHS Secretary Tommy G. Thompson allowed it to take effect as scheduled, with compliance for most covered entities required by Apr. 14, 2003. (Small health plans have an additional year.) In March 2002, HHS proposed specific changes to the privacy rule to ensure that it protects privacy without interfering with access to care or quality of care. After considering public comments, HHS issued a final set of modifications on Aug. 14, 2002. Most covered entities were required to comply with the privacy rule by Apr. 14, 2003; small health plans had until Apr. 14, 2004 to come into compliance, as required under the law. Detailed information about the privacy rule is available at www.cms.gov/hipaa/hipaa2/enforcement.

In February 2003, HHS adopted final regulations for security standards to protect electronic health information systems from improper access or alteration. Under the security standards, covered entities must protect the confidentiality, integrity and availability of electronic protected health information. The rule requires covered entities to implement administrative, physical and technical safeguards to protect electronic protected health information in their care. The standards use many of the same terms and definitions as the privacy rule to make it easier for covered entities to comply. Most covered entities must comply with the security standards by Apr. 21, 2005, while small health plans have an additional year to come into compliance.

Privacy and security standards promote higher quality care by assuring consumers and/or patients that their health information will be protected from inappropriate uses and disclosures. In addition, uniform national transaction and code set standards will save billions of dollars each year for health care businesses by lowering the costs of developing and maintaining software and reducing the time and expense needed to handle health care transactions.

SUMMARY OF THE INVENTION

What is needed is a comprehensive electronic data management system that allows entities concerned with improving information privacy or impacted by privacy legislation, such as, but not limited to, the HIPAA, PIPEDA and other privacy or security rules and regulations, to readily address privacy concerns. Although such a system will be of special advantage to those in the healthcare industry, the disclosed system has application in other fields as well. By way of example, without intending to limit the present invention, the system can be deployed in the banking, financial and insurance industries. Also by way of example, without intending to limit the present invention, it can be used to deploy or bring to compliance database systems where extensive and accurate audit trails are mandatory due to legislation, insurance, industry trade groups, or motivators other than privacy, e.g. Sarbannes-Oxley in the Securities industry. Accordingly, the present invention is directed to a data access management system that substantially obviates one or more of the problems due to limitations and disadvantages of the related art.

In one embodiment the invention provides an information management system for restricting access to personal data in compliance with law or regulation. The system includes a database having restricted records stored therein, at least one of the records including an identification of a client or group of clients about whom said record concerns. A computer system under the control of a trusted information broker is configured to receive via a communication medium a request initiated by a requestor for access to at least one of the restricted records in the database, the request including an identification of the requestor. The computer system is further configured to transmit a request for consent to the client and receive an indication from the client that the client consents or does not consent to access to the restricted record by the requestor. The computer system grants or denies access to the restricted records based upon the indication from the client.

An embodiment of the invention is preferably directed to the creation of a trusted information broker, also referred to herein as a "TIB", which gives patients, or others about whom private information is collected, the ability to give express consent and the power to control access to the information, and to review and edit the information. An extension of the role of the TIB would be to become a trusted information custodian (TIC); in this role, the TIB/TIC would also host the private information gathered by health care providers and other authorized individuals. Hospitals, health care providers, and other information sources can transmit information collected locally by them at the TIC to the trusted information broker, where it is made available to other health care providers and authorized individuals based on the patient's preferences.

Another embodiment of the invention is directed to the creation of a local TIB and/or TIC within the settings of health care providers and other authorized individuals. Hospitals, health care providers, and other information sources can collect and store information locally by them, where it is made available to other health care providers and authorized individuals based on their local legislations and practices.

As patients or other types of clients are entered into the system, and as various events occur, they can pre-authorize certain entities, such as health insurance companies, hospitals, emergency room physicians, or the like to have access to some or all portions of the client's confidential records. For example, patients can give their family doctor and emergency room physicians easy access to all healthcare related information, while restricting an endocrinologist's access to only certain records, or records from certain sources. By giving patients the control over their data, patients can make more informed healthcare choices. At the same time, because the system in one embodiment can provide a central repository for all healthcare related information, the present invention can aid health care providers in giving their patients better care by giving the providers access to a wider range of information, and by making certain information available in a real-time manner.

It is to be understood that both the foregoing general description and the following detailed description are exemplary and explanatory and are intended to provide further explanation of the invention as claimed. Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of at least one embodiment of the invention.

In the drawings.

DETAILED DESCRIPTION OF THE PREFERRED EMBODIMENT

Reference will now be made in detail to the preferred embodiments of the present invention, examples of which are illustrated in the accompanying drawings.

As described above, certain embodiments of the present invention are directed toward a medical record information management system. However, the invention has applications outside the medical field, and can be used to permit any type of service provider or other requestor to access information, particularly confidential or private information, about a client. Such applications include, e.g., systems employed by government agencies (such as Homeland Security and HHS) and financial institutions to provide restricted access to personal information. As such, although the description of the embodiments of the invention contained herein uses terms such as patient and doctor, it should be apparent to one skilled in the art that such terms include other types of client or service provider, respectively, in a more generic embodiment.

Figure 1:
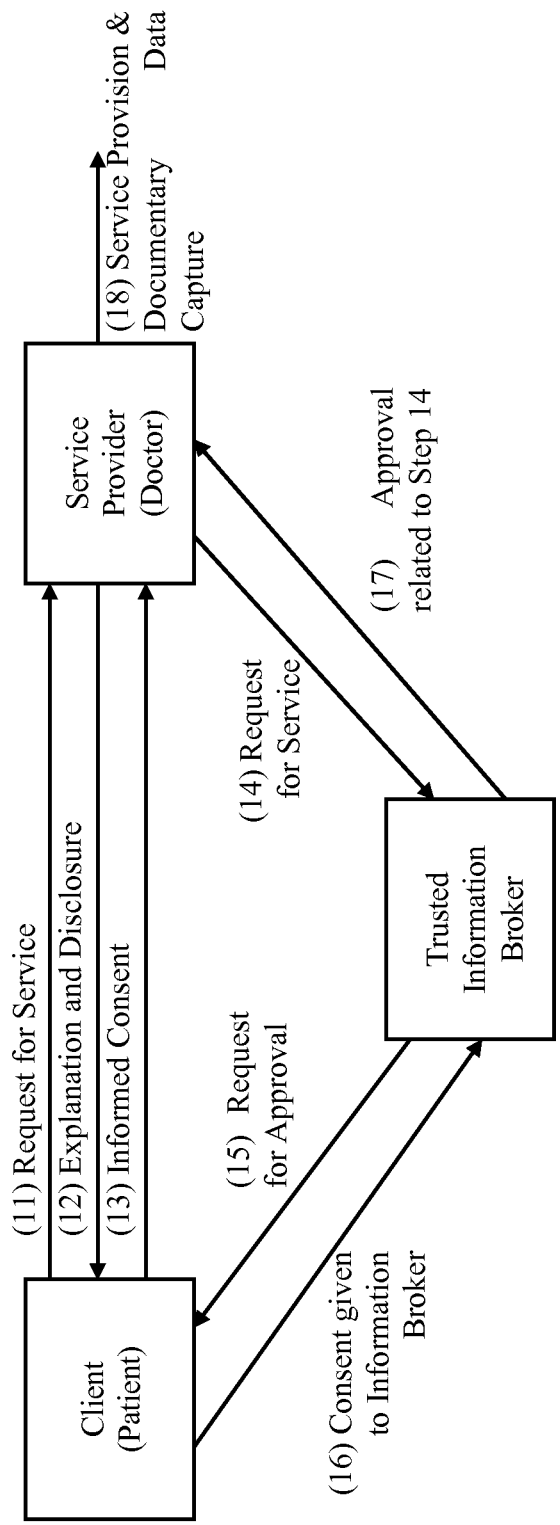
FIG. 1 is a flow chart illustrating a consent capture data flow.

FIG. 1 is a flow chart illustrating a consent capture data flow. This process preferably begins at Step 11, in which a client requests service from a service provider. Communications between clients, service providers, and the trusted information broker are preferably encrypted. In one embodiment, such encryption is implemented as a 128 bit symmetric key which is uniquely generated for each communication session. Although a 128 bit symmetric key is presently preferred, alternative key lengths may be substituted therefor without departing from the spirit or the scope of the invention. Encryption may take place using any well known encryption algorithm, including, without limitation, the Advanced Encryption Standard (AES), Data Encryption Standard (DES), Triple-DES, and Skipjack algorithms. AES has the added advantage of being the National Institutes of Standards and Technology's Federal Information Processing Standard (FIPS) approved symmetric encryption algorithm of choice, thus making it the preferred algorithm for use in conjunction with HIPAA. Federal Information Processing Standards Publication 197 describes the AES algorithm and its implementation.

In Step 12, the service provider explains the services to be provided, the information to be collected about the client as part of the service, and information to which the service provider will need access to be able to provide the service. The client then provides their consent to the service as part of Step 13.

In Step 14, the service provider requests information from a trusted information broker. The trusted information broker can manage access to information about a variety of clients. Information to which the trusted information broker has access includes information stored locally by the trusted information broker, as well as information stored at any given service provider site. As will be appreciated by one skilled in the art, distributed information storage may be advantageous in some embodiments, as such systems limit the information available to untrusted parties, such as hackers. By not storing all client information in a single location, the hacker is inherently limited to only the information maintained by a given service provider.

When the trusted information broker receives the service request as part of Step 14, if the service provider is not preauthorized to access the information, the trusted information broker sends a request to the client to permit the service provider to access the information. Clients can select the level of detail to be included in such a request, ranging from generic, category-level descriptions of the information, to detailed, record-specific descriptions of the information. This request is transmitted as part of Step 15.

In one embodiment, the client can deny the request, approve the entire request, or selectively grant and deny portions of the request. By way of example, without intending to limit the present invention, if a service provider's request would grant access to psychological test results where such results are not needed by the service provider, in such an embodiment the client can deny the service provider access to the psychological test results while granting access to the other information requested.

The client's approval/rejection of the request is transmitted back to the trusted information broker as part of Step 16. In Step 17, the service provider is advised of the results of the information request made in Step 14, and is given access to any information to which the service provider has been granted access. In Step 18, the service provider provides services to the client, and captures additional information.

Figure 2:
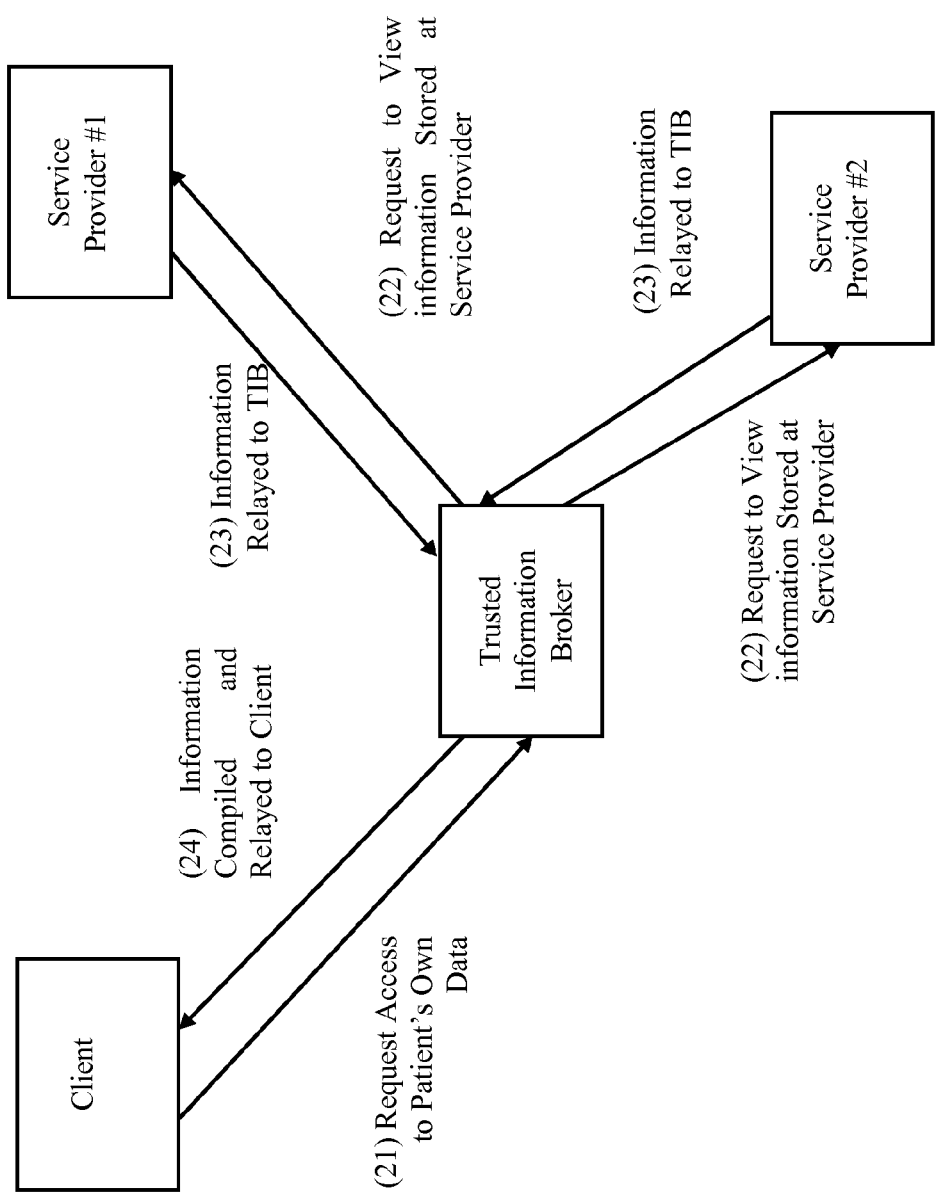
FIG. 2 is a flow chart illustrating a client data access flow.

Information captured as part of Step 18 can be stored at the trusted information broker, stored at the service provider, distributed in a secure manner across service providers, or any combination thereof. This is illustrated in part by FIG. 2. In FIG. 2, the trusted information broker may obtain information about the client from Service Provider 1, encrypt such information, and store the encrypted information with Service Provider 2. This provides a distributed, redundant storage mechanism that greatly increases overall system reliability.

FIG. 2 is a flow chart illustrating a client data access flow. In Step 1 of FIG. 22, the client requests access to their own data from the trusted information broker. The trusted information broker determines the data to be presented to the client and, if such data is stored outside the trusted information broker, a request for such information is sent to each service provider or other entity storing such information as part of Step 22.

Each entity returns the information to the trusted information broker as part of Step 23. The trusted information broker consolidates the information and presents it to the client as part of Step 24.

Figure 3:
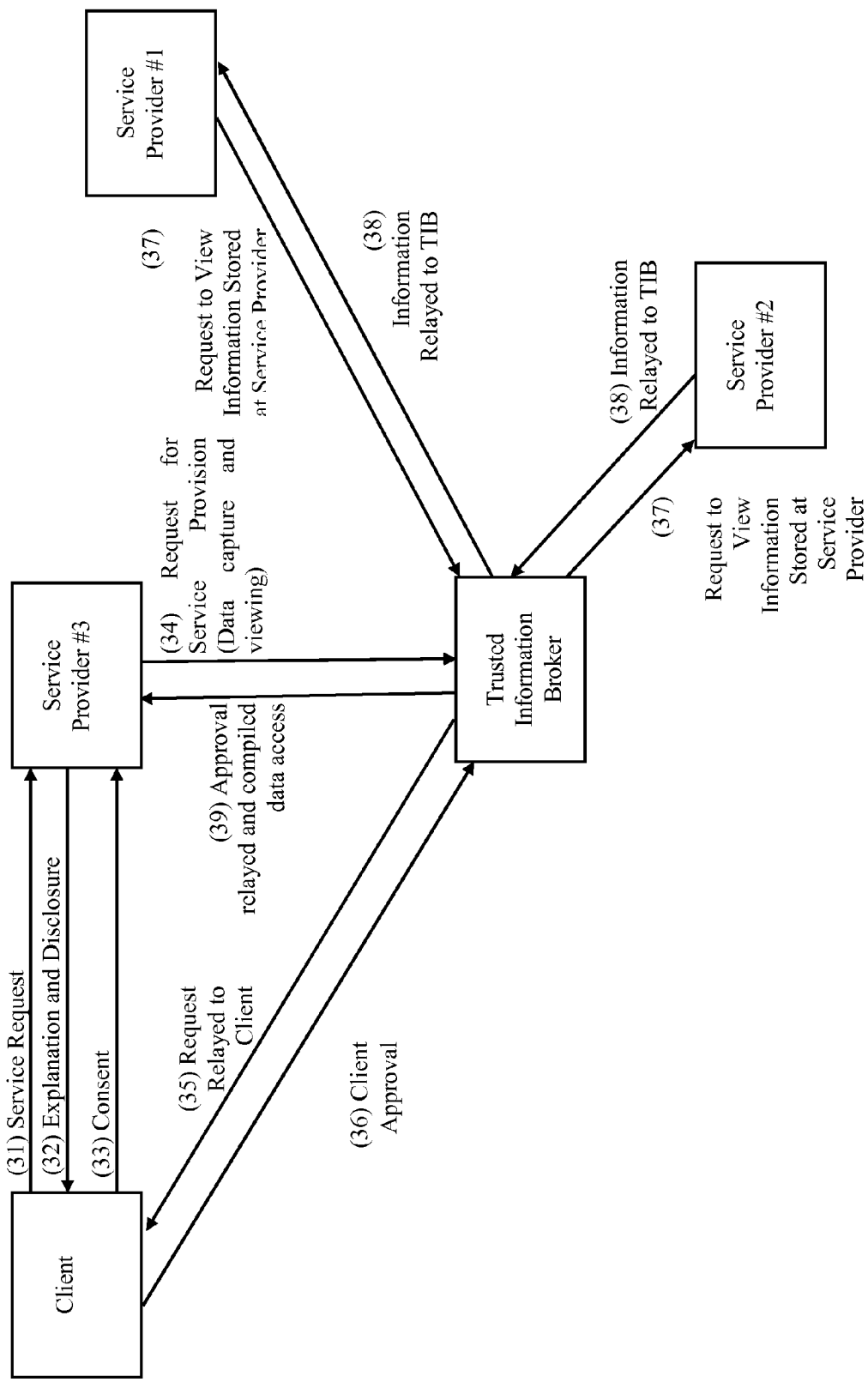
FIG. 3 is a flow chart illustrating a service provider data access flow.

FIG. 3 is a flow chart illustrating service provider data access flow. In FIG. 3, a client requests service from service provider 3 as part of Step 31. In Step 32, service provider 3 explains the services to be provided, the information to be collected about the client as part of the service, and information to which the service provider will need access to be able to provide the service, as described above with respect to FIG. 1. In Step 33, the client consents to the service provider performing the service. Service Provider 3 then indicates to the trusted information broker that it is to provide certain services, and lists the data to be captured and the data to which the service provider will need access. The trusted information broker consolidates this information and presents it to the client as part of Step 35. As described in more detail above with respect to FIG. 1, the client can accept or reject portions or all of the service provider's request as part of Step 36. If service provider 3's request includes information that is not stored at either service provider 3 or the trusted information broker, the trusted information broker can request the information from other service providers as part of Step 17. In Step 18, the information is provided to the trusted information broker, which in turn relays the client's approval and the compiled data to service provider 3.

Figure 4:
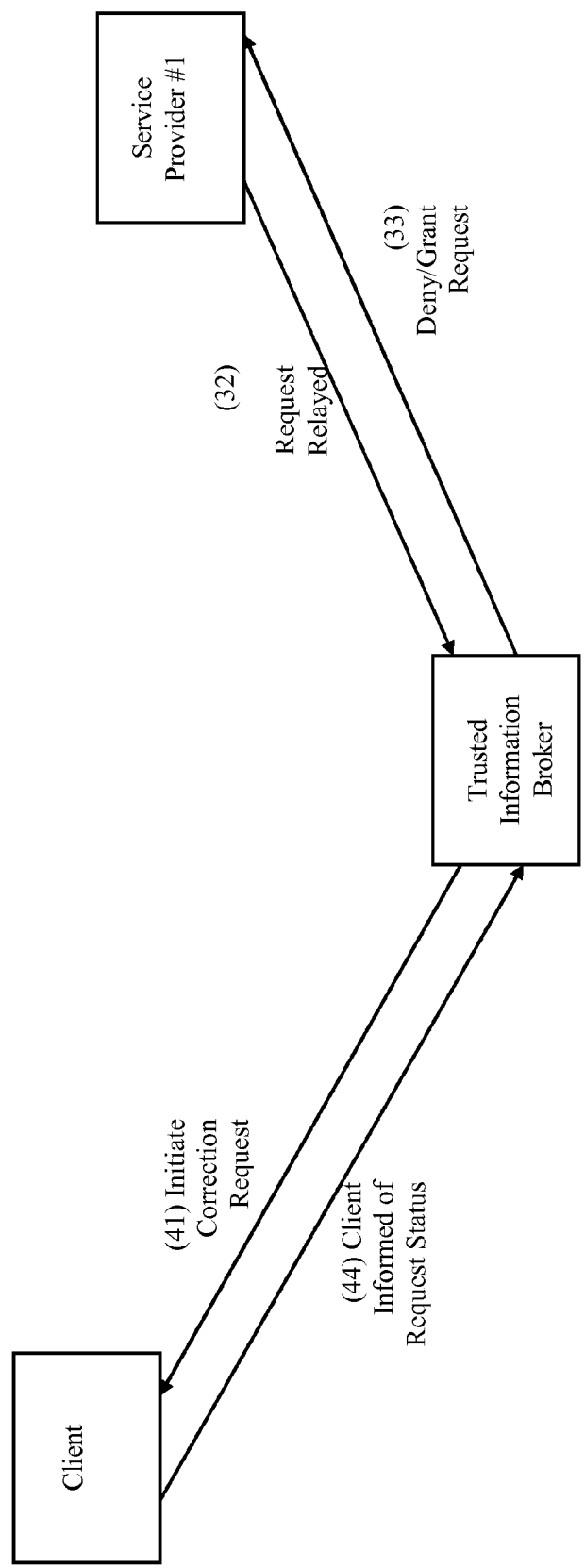
FIG. 4 is a flow chart illustrating a preferred client data correction flow.

FIG. 4 is a flow chart illustrating a preferred client data correction/change flow. In FIG. 4, the client initiates a data correction/change request as part of Step 41. In Step 42, the trusted information broker transmits the request to the service provider. In a preferred embodiment, since the information about the client is deemed to be owned by the client, the service provider should record the changes. However, in some cases, the service provider may disagree with the change being made, such as where the change is to a substantive portion of the client's record. In such cases, the service provider may then deny the request. The grant or denial of the request is transmitted to the trusted information broker as part of Step 43.

In a preferred embodiment, all data maintained by the present invention is permanently stored. Access to certain records may be controlled, and certain records may be marked as inactive or deleted, but the records are preferably never removed.

Furthermore, all transactions, such as, but not limited to, data access and data correction requests, and the results thereof, are preferably logged by the trusted information broker, thereby creating an audit trail. Such logging preferably includes a record of the transaction which is digitally signed by the entity performing the transaction. With respect to logging data correction transactions, in the case where a service provider refuses to change information in a client's record, the trusted information broker can record the dispute and the differing versions of the record, and can make both versions available to other service providers.

This audit trail capability can be particularly advantageous in implementations of the system in financial and other institutions where access to confidential information (e.g., credit card numbers, bank account numbers, other account numbers, passwords, personal biographical information, criminal records or other law enforcement records, records of minors, etc.) must, by law, be limited and/or logged. The audit trail capability of the system is further particularly useful for applications of the invention to limit government access to data records. The invention may be implemented to limit and log access to classified or restricted-access information from disparate systems, including systems at one or more government agencies. The audit trail feature of the invention may be used to create a log of any parameter associated with a record access transaction or record change transaction. Such parameters include, e.g., an identification of the person requesting the transaction, an identification of the agency requesting the transaction, the date of the transaction, reasons listed for viewing the restricted information, particular documents or records accessed, and any changes made to records.

As illustrated by Step 44 of FIG. 4, the trusted information broker preferably informs the client of the change request status. Clients can also contact the service provider to negotiate any rejected changes.

Figures 5A, 5B:
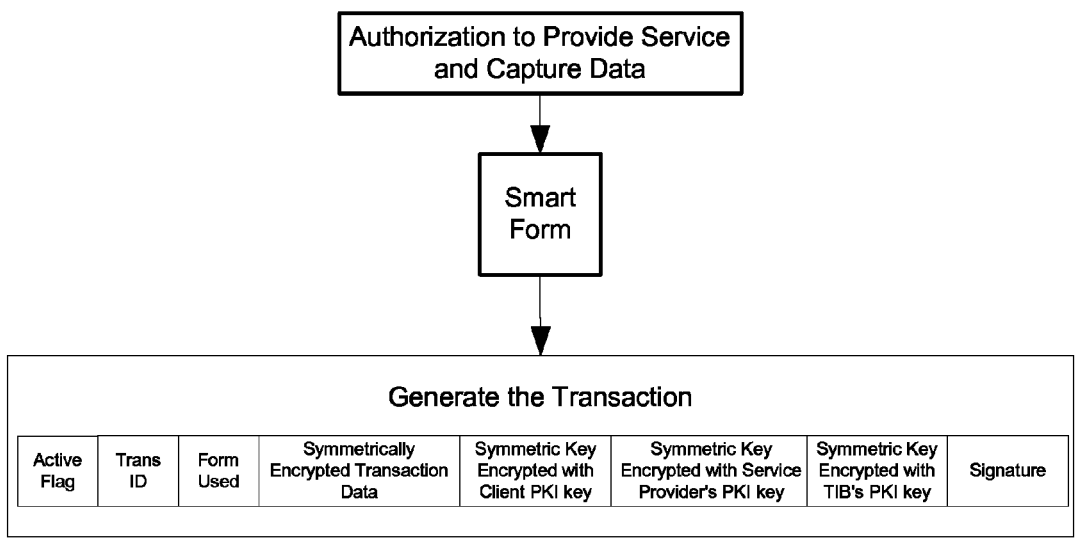
FIGS. 5a and 5b are block diagrams illustrating fields in exemplary data records.

The present invention implements the data flow processes described above utilizing a flexible, extensible architecture. At the heart of this architecture is a database which has been designed from the ground up with security and privacy in mind. FIGS. 5a and 5b are block diagrams illustrating fields in exemplary data records. As described above, each transaction is stored as a database record by the present invention. By way of example, without intending to limit the present invention, in a medical embodiment, as a physician enters the results of a patient's most recent visit, this information is stored in the present invention in the form of one or more database records. Such records are preferably stored in a database at the physician's office, thus allowing the physician to easily access the information on the patient's next visit. The information can also be stored as part of a central database maintained by the present invention.

As illustrated in FIG. 5a and described above, a symmetric key is generated and used to encrypt communications between the trusted information broker and the service provider. This symmetric key is transmitted to the service provider as part of the authorization to provide service a service provider receives from the trusted information broker. The data is encrypted by the service provider prior to transmission to the trusted information broker. The encrypted information is stored in a transaction record, to which a transaction ID is also assigned. The transaction record also preferably includes an active flag, and a record of the form used by the service provider in entering the encrypted data. The transaction record also preferably includes a copy of the symmetric key which has been asymmetrically encrypted with the patient's public key using encryption techniques such as, but not limited to, those commonly referred to as Public Key Infrastructure, or PKI. The transaction record also preferably includes a copy of the symmetric key which has been asymmetrically encrypted with the service provider's public key, and a copy of the symmetric key which has been asymmetrically encrypted with the trusted information broker's public key. The transaction is also preferably digitally signed by the entity executing the transaction, and this signature is preferably stored in the transaction record.

The database record architecture illustrated in FIG. 5a has the advantage of creating a very secure set of database records which are readily accessible to all parties entitled to access the records. In addition, the architecture allows the trusted information broker to access the information on behalf of service providers who are not the creators of the data, thereby creating an extensible data access environment.

FIG. 5b illustrates an alternative database record architecture. In the embodiment illustrated in FIG. 5b, the symmetrically encrypted transaction data is stored in a database along with a transaction identifier, form information, and an active flag. A separate database or database table is used to store a reference to the transaction identifier, the symmetric key encrypted with the patient's PKI public key, the symmetric key encrypted with the trusted information broker's PKI public key, and the public keys for any service providers permitted to access the transaction data. This provides a more distributed data storage architecture, thereby allowing the transaction-specific information to be stored, for example, at a service provider, while the access-specific information is stored by the trusted information broker. This architecture has the advantage of preventing anyone who gains unauthorized access to the service provider's computer from accessing client information without authenticating with the trusted information broker.

In still another embodiment, the symmetric key can be encrypted using the client's public key, and the result of this encryption can be further encrypted using the trusted information broker's public key. Such an embodiment may be advantageous, for example, where the information stored is of such a nature that the client wishes to limit even the trusted information broker's access to the information. By way of example, without intending to limit the present invention, such information may include records involving legal proceedings regarding the client that were undertaken while the client was a minor. Such records are typically sealed, and require the client's consent or a judicial order before they can be opened. The layered encryption approach of this embodiment is advantageous because it would require the client's private key before the trusted information broker can access the information.

Figure 6:
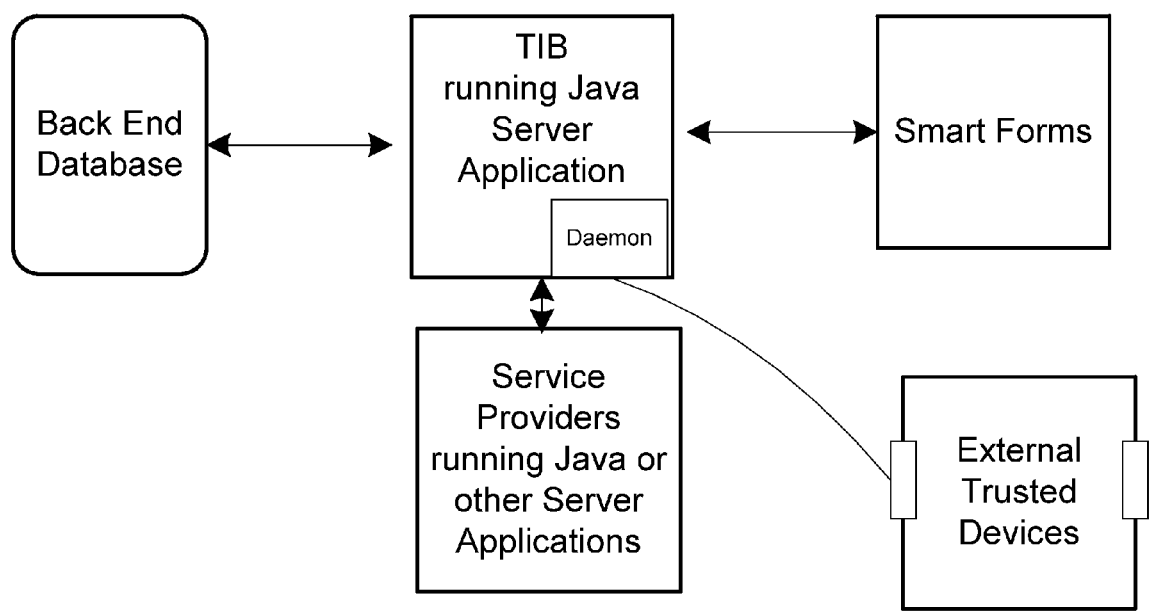
FIG. 6 is a block diagram illustrating a preferred system architecture.

FIG. 6 is a block diagram illustrating a system architecture for implementing the trusted information broker. The illustrated embodiment uses open-source software. However, as will be apparent to one skilled in the art, proprietary operating systems, server software, database software, and the like can be substituted for the components described herein without departing from the spirit or the scope of the invention.

The trusted information broker is preferably implemented as one or more web-based services which utilize secure communication channels between the various entities and the trusted information broker. Such communication channels may be implemented using any of a variety of well known communications protocols, including, but not limited to, Secure Socket Layer (SSL), Virtual Private Network (VPN), Internet Protocol Security (IPSec), and the like.

Although such communication channels are useful for protecting data in transit between entities, they do not protect stored data. By way of example, without intending to limit the present invention, SSL sits on top of the HyperText Transport Protocol (HTTP), which uses simple uniform resource locators (URL's) to access data. In such typical configurations, two parties using the same URL, even across different SSL sessions, will access the same information. Still further, not all devices used with, and embodiments of, the trusted information broker take advantage of secure communication channels. Thus, to add another layer of security, the present invention preferably masks critical identification parameters using session scoped volatile strings of randomly generated characters. This is generally referred to herein as "obfuscation".

To implement the obfuscation, a string of random characters masks each communication parameter. The random characters are appended to or otherwise associated with a URL, and the complete URL is necessary to communicate with the trusted information broker. When the communication session is closed by the trusted information broker, the random characters are discarded, as are all associations between the random characters and the underlying data.

As should be apparent to one skilled in the art, the trusted information broker may be implemented using a variety of languages. In the embodiment illustrated in FIG. 6, the trusted information broker is implemented in a JAVA runtime environment. This implementation is preferred as it allows for platform-neutral implementations which are readily scalable and can be enhanced to accommodate increased bandwidth, transactional, and processing needs. As FIG. 6 illustrates, the computer or computers on which the trusted information broker is implemented can also communicate in real-time or in batch mode with enabled external trusted devices. By way of example, without intending to limit the present invention, this can allow biometric identification (security applications), monitoring sensors (such as cardiovascular monitors and glucometers) and the like to access and store data.

The back end database is preferably implemented using a Relational Database Management System (RDBMS). By way of example, without intending to limit the present invention, MySQL may be used, although alternative database server software can be substituted therefor without departing from the spirit or the scope of the invention. In addition to storing the transaction records described above, the back end database also stores client-specific information, including, but not limited to, access control lists generated by and/or pertaining to the client. Such access control lists allow clients to identify individual service providers, groups of service providers, and others who should be explicitly granted or denied access to client information. These lists are used by the system when determining whether a given service provider has been previously granted access to client data and whether such access should be granted for a given request.

The smart forms are preferably Health Level 7 (HL7) compliant forms for exchanging data between service providers. Information on the Health Level 7 standards are well-known and can be obtained, e.g., from www.HL7.org. The smart forms also preferably include field identifiers that indicate which fields are likely to include private information and which fields include public information. By flagging such data as it is entered, the trusted information broker can strip out any private information while still allowing research groups and the like to mine data stored in the trusted information broker, thereby facilitating research.

The smart forms are preferably used for both data input and presentation. The smart forms preferably determine, based on access control lists, the information that a service provider or other user can view.

Figure 7:
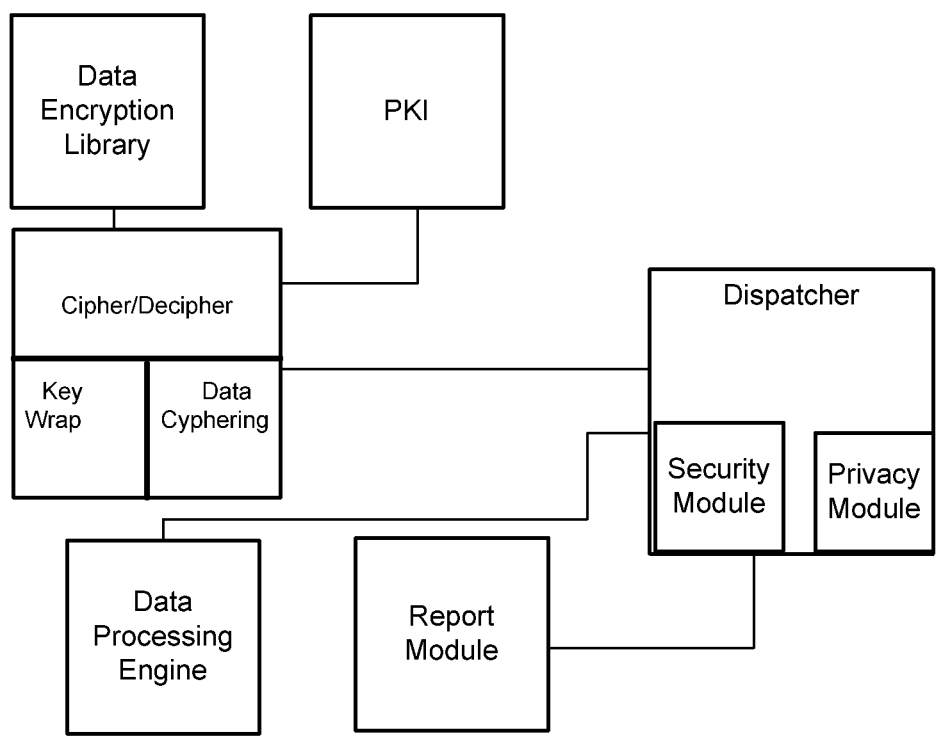
FIG. 7 is a block diagram illustrating various modules of the system.

FIG. 7 is a block diagram illustrating various modules of the trusted information broker. The heart of the trusted information broker is the dispatcher module. The dispatcher is responsible for managing communication between the various modules, and with external entities. Because security and privacy considerations are high priority within a preferred embodiment of the invention, the security and privacy modules are preferably integral parts of the dispatcher module.

The security module is responsible for user authentication, data integrity, confidentiality, non-repudiation, and access control list creation and enforcement. The access control list enforcement is preferably implemented by limiting the information available based on the group to which a given user belongs, and context in which the user is accessing the information. By way of example, without intending to limit the present invention, a surgeon, in his role as a client, is preferably allowed to view any or all medical records pertaining to himself and his medical history, while the same surgeon is preferably limited to viewing only those medical records to which he has access that pertain to another client, and to entering new records for clients who have given authorization for the surgeon to create such records. The privacy module is responsible for enforcing data ownership, logging data access for accountability, obtaining and enforcing client consent, and verifying the accuracy of information entered concerning a given client.

The Cipher/Decipher module handles the encryption and decryption of information, as well as the generation of symmetric keys. The data encryption library is preferably a modular library design which allows new encryption algorithms to be readily added to the trusted information broker. The PKI module allows the trusted information broker to leverage a public key encryption architecture to further enhance overall security and allow for proper authentication and non-repudiation.

The report module is responsible for preparing visual presentations of the information a given user can view. The report module includes, but is not limited to, functionality for processing data in the smart forms described above.

The following is an example of the interaction of the various modules. The example is intended for illustrative purposes only, and should not be construed as limiting the invention. When a user first attempts to log into the system, the dispatcher's login process calls the security module. The security module attempts to authenticate the user (via the chosen mode of authentication, e.g. PKI) and, if successful, the system returns a login token. The user can then review a list of clients whose information the user is authorized to view. For most clients, this list will simply include the user himself; however, for service providers, this is likely to be a set of clients.

Figure 8:
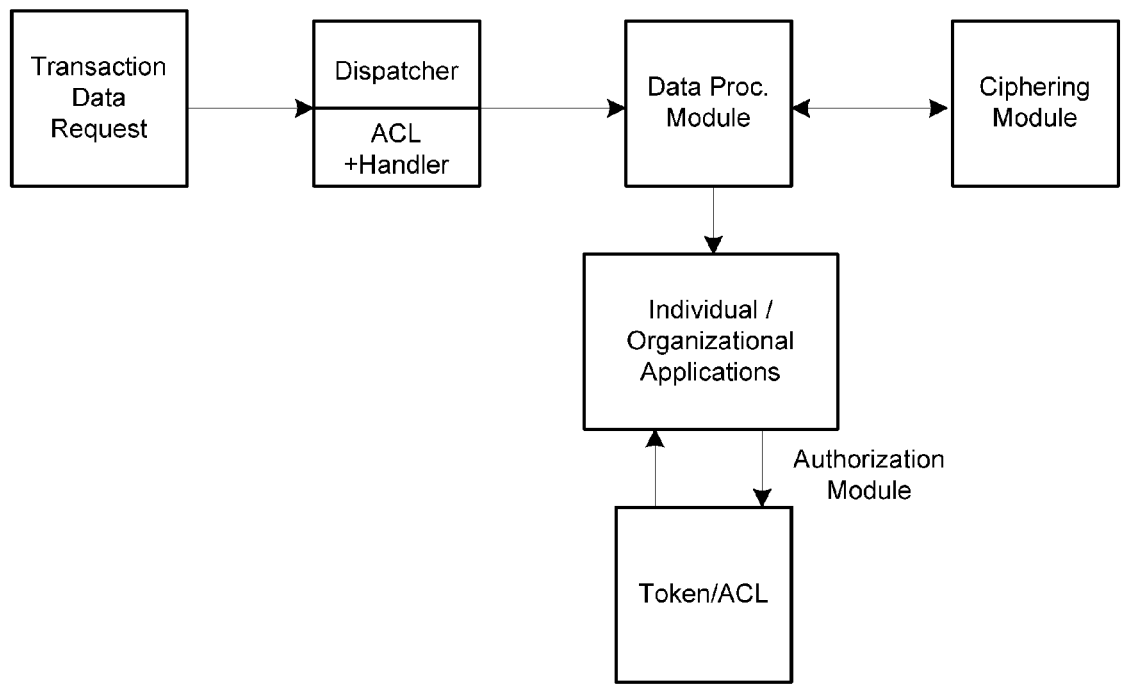
FIG. 8 is a block diagram illustrating interaction of system modules.

FIG. 8 provides an illustrative example of the interaction of the modules when a user requests information. Again, this example is intended for illustrative purposes only, and should not be construed as limiting the invention. As the user requests data, the requests are processed by the dispatcher. The dispatcher validates the user via the security and privacy modules using the login token. Assuming the login token is valid, the dispatcher determines the groups to which the user has been assigned based on the access control lists stored in the trusted information broker, and ultimately determines the user's access rights. The dispatcher creates a "handler" instance for the information request, which preferably includes the information requested by the user, the user's access control list ("ACL"), and other such information. The dispatcher forwards the handler and the login token to the data processing module. The data processing module verifies the user's ACL and handler, then calls the ciphering module, which unwraps the symmetric key, and subsequently unlocks the transaction data. The transaction data is passed back to the data processing module as part of the handler, and the data processing module applies the ACL using individual and organizational applications to limit the information available to the user to only that which the user is authorized to view. This is passed to the dispatcher, which passes the data to an appropriate smart form.

While the invention has been described in detail and with reference to specific embodiments thereof, it will be apparent to those skilled in the art that various changes and modifications can be made therein without departing from the spirit and scope thereof. Thus, it is intended that the present invention cover the modifications and variations of this invention provided they come within the scope of the appended claims and their equivalents.

The embodiments of the invention in which an exclusive property or privilege is claimed are defined as follows:

1. A medical record information management system, comprising:
   a database having stored therein a plurality of medical records, each medical record including an identification of a corresponding client, each medical record further including individual transaction records, each separately and uniquely encrypted before storage in said database, whereby ownership of each individual transaction record is implemented in the data record itself;
   a computer system under the control of a third party trusted information broker, said computer system being configured to receive via a communication medium a first request initiated by a service provider for access to at least one of said medical records in said database, said first request including an identification of the service provider;
   said computer system being further configured to transmit a request for consent to said client and receive an indication from said client that said client consents or does not consent to access to said medical record by said service provider;
   said computer system being further configured to grant or deny access to said at least one client record based upon said indication from said client;
   said computer system being further configured to receive a second request initiated by a second service provider to enter at least one second transaction record to said database, and to receive a third request initiated by a third service provider to enter at least one third transaction record to said database, each service provider being an external entity not affiliated with the third-party trusted information broker.

2. The medical record information management system in accordance with claim 1, wherein said computer system is further configured to selectively grant or deny portions of the first request.

3. The medical record information management system in accordance with claim 1, wherein said computer system is further configured to consult an access control list to determine whether said service provider is pre-authorized to view a requested record.

4. The medical record information management system in accordance with claim 3, wherein said access control list includes an indication of a group to which said service provider belongs, and wherein said computer system is configured to grant or deny access to said requested record based upon a group to which the service provider belongs.

5. The medical record information management system in accordance with claim 1, wherein said computer system is configured to grant or deny access to said requested record based upon a context in which said service provider is accessing the information.

6. The medical record information management system in accordance with claim 1, wherein communication between said computer system and said service provider is encrypted.

7. The medical record information management system in accordance with claim 1, wherein communication between said computer system and said client is encrypted.

8. The medical record information management system in accordance with claim 1, wherein communication between said computer system and at least one of said client or said service provider is encrypted using a key which is uniquely generated for each communication session.

9. The medical record information management system in accordance with claim 1, wherein communication between said computer system and at least one of said client or said service provider is conducted via a secure communication channel.

10. The medical record information management system in accordance with claim 9, wherein said secure communication channel comprises at least one of: Secure Socket Layer (SSL), Virtual Private Network (VPN), or Internet Protocol Security (IPSec).

11. The medical record information management system in accordance with claim 1, wherein the computer system is further configured to maintain an audit trail of access to or changes to at least one of said plurality of records.

12. The medical record information management system in accordance with claim 11, wherein said audit trail includes at least one transaction log which is digitally signed.

13. The medical record information management system in accordance with claim 11, wherein said audit trail includes at least one transaction log that includes a transaction parameter.

14. The medical record information management system in accordance with claim 13, wherein said transaction parameter includes at least one of: an identification of a person requesting the transaction, an identification of an agency requesting the transaction, a date of the transaction, reasons listed for viewing the said record, an identification of particular documents or records accessed, or changes made to said record.

15. The medical record information management system in accordance with claim 1, wherein the computer system is further configured to transmit or receive data in electronic forms that include field identifiers indicating which fields include private information and which fields include public information.

16. The medical record information management system in accordance with claim 1, wherein the computer system is further configured to: authenticate a user logging into the system, issue a login token to said user, transmit to said user a list of clients whose information the user is authorized to view, determine one or more groups to which the user has been assigned based upon one or more access control lists, determine the user's access rights, create a handler instance for an information request from said user, unwrap a symmetric key and subsequently unlock transaction data, pass transaction data to a data processing module, use the data processing module to apply said one or more access control list to limit the information available to the user to only that which the user is authorized to view, pass the information to a dispatcher, and use the dispatcher to pass the data to an appropriate smart form.

17. The medical record information management system in accordance with claim 1, wherein said database resides with said trusted information broker.

18. The medical record information management system in accordance with claim 1, wherein said database resides with said service provider.

19. The medical record information management system in accordance with claim 1, wherein said database comprises one or more databases distributed across multiple geographic locations.

20. The medical record information management system in accordance with claim 1, wherein said request for access includes an identification of services to be provided and an identification of information to which the service provider will need access to be able to provide said service.

* * * * *